US011707602B2

(12) United States Patent
Shendelman (10) Patent No.: US 11,707,602 B2
(45) Date of Patent: Jul. 25, 2023

(54) CATHETER SYSTEM

(71) Applicant: Leonid Shendelman, Brooklyn, NY (US)

(72) Inventor: Leonid Shendelman, Brooklyn, NY (US)

( * ) Notice: Subject to any disclaimer, the term of this patent is extended or adjusted under 35 U.S.C. 154(b) by 454 days.

(21) Appl. No.: 16/555,111

(22) Filed: Aug. 29, 2019

(65) Prior Publication Data

US 2021/0060300 A1  Mar. 4, 2021

(51) Int. Cl.
  *A61M 25/02*  (2006.01)
  *A61M 25/00*  (2006.01)
  *A61M 25/10*  (2013.01)

(52) U.S. Cl.
  CPC ........ *A61M 25/02* (2013.01); *A61M 25/0023* (2013.01); *A61M 25/10* (2013.01);
  (Continued)

(58) Field of Classification Search
  CPC .. A61M 25/02; A61M 25/0023; A61M 25/10; A61M 2025/0024; A61M 2025/0206; A61M 2205/0222; A61M 2210/1085; A61M 27/00; A61M 25/0017; A61M 2025/0046; A61M 25/0045; A61M 2025/006; A61M 2025/1086; A61M 25/007; A61M 2025/105; A61M 2210/1089; A61M 2202/0496; A45F 5/00; A45F 2003/166; A45F 2005/008; A45F 3/16; A45F 2003/045; A61J 1/2089; A61J 1/1412; A61J 1/201; A61J 1/2055;
  (Continued)

(56) References Cited

U.S. PATENT DOCUMENTS

| | | | | |
|---|---|---|---|---|
| 3,428,046 A | * | 2/1969 | Vagenius | A61L 29/043 607/40 |
| 4,057,062 A | * | 11/1977 | Lavigne | A61F 5/4405 604/326 |
| 5,460,606 A | * | 10/1995 | Daneshvar | A61M 25/02 604/326 |
| 5,865,821 A | * | 2/1999 | Lowey | A61F 5/4408 604/352 |

(Continued)

FOREIGN PATENT DOCUMENTS

| | | | | |
|---|---|---|---|---|
| EP | 0795339 A1 | * | 9/1997 | ........ A61M 25/0069 |
| GB | 2153231 A | * | 8/1985 | ............... A61F 5/44 |

OTHER PUBLICATIONS

Hutzler, "Drainage Catheter", Sep. 17, 1997, PGPUB Translation (Year: 1997).*

*Primary Examiner* — Kai H Weng
*Assistant Examiner* — Brandon W. Levy
(74) *Attorney, Agent, or Firm* — Ryder, Mazzeo & Konieczny LLC; Joseph M. Konieczny, Sr.

(57) ABSTRACT

A catheter system includes an indwelling, hollow catheter having a tip inserted into a person's bladder. The tip has an opening through which urine from the bladder passes into the catheter. A flexible reservoir extends around the person's ankle and has walls bounding an interior compartment. A flexible, elongated tube has one end connected to the catheter and an opposite end connected to the reservoir. The tube is hollow for conducting urine in the catheter through the tube into the compartment of the reservoir. One of the walls of the reservoir is a bottom wall that engages and rests on a top of the person's foot in use to resist downward movement of the reservoir as the reservoir is filled with urine. A freely manipulated drain pipe is in fluid communication with the reservoir.

24 Claims, 9 Drawing Sheets

(52) U.S. Cl.
CPC ............... *A61M 2025/0024* (2013.01); *A61M 2025/0206* (2013.01); *A61M 2205/0222* (2013.01); *A61M 2210/1085* (2013.01)

(58) Field of Classification Search
CPC .......... A61J 1/2051; A61J 1/10; A61J 1/2013; A61F 5/4408; A61F 5/453; A61F 5/4404; A61F 5/455; A61F 2250/0067; A61F 13/28; A61F 2/95; A61B 10/007; A61B 1/00; A61B 5/0215; A61B 2017/22092; A61B 2018/00142; A61B 17/50; A61B 10/02; A61B 10/0045; G02B 23/24; A61D 1/12; A61D 7/00; A61H 19/40
See application file for complete search history.

(56) References Cited

U.S. PATENT DOCUMENTS

| | | | |
|---|---|---|---|
| 6,659,996 B1 * | 12/2003 | Kaldany | A61M 37/0069 604/509 |
| 6,736,803 B2 * | 5/2004 | Cawood | A61F 5/4405 604/327 |
| 2008/0281284 A1 * | 11/2008 | Garfield | A61F 5/44 604/327 |
| 2008/0284163 A1 * | 11/2008 | Proulx | A61M 39/12 285/242 |
| 2011/0251572 A1 * | 10/2011 | Nishtala | A61F 5/44 604/326 |
| 2015/0051588 A1 * | 2/2015 | Miller | A61M 39/1055 604/544 |
| 2017/0020369 A1 * | 1/2017 | Nishina | G02B 23/24 |

\* cited by examiner

CATHETER SYSTEM

FIELD OF THE INVENTION

The present invention relates generally to a catheter system.

BACKGROUND OF THE INVENTION

People dealing with urinary incontinence often require, for either short term (up to two weeks or less) usage or long term (greater than two weeks up to about three months or more) usage, an indwelling catheter, typically a Foley catheter, connected to an exterior urine collection and drainage bag or reservoir. Mobile and active people, male or female, who have to wear such a reservoir on their bodies, are faced with a number of challenges, such as undesired reservoir and/or catheter movement, urine leakage, discomfort during insertion of the catheter through the person's urethra and into the bladder, irritation and soreness of the urethra and the bladder especially over long term use, undesired enlargement of and potential damage to the urethral passage, wardrobe issues, and difficulty of urine drainage from the reservoir, just to name a few such challenges.

The known reservoir is customarily attached to the person's thigh or upper leg, by one or two straps, and is connected to the indwelling catheter by a plastic, hollow, flexible tube through which the urine passes and flows from the catheter to the reservoir. As urine collects in the reservoir, its increased weight may pull on the catheter. For example, a reservoir filled with about 500 milliliters (about 1 pint) of urine weighs about half a kilogram (about 1 pound). Such a weighted reservoir may cause discomfort and irritation to the delicate tissue of the urethra and bladder especially over long term usage, and may also pull the catheter down and cause the connections of the tube to the catheter and the reservoir to loosen and disengage, thereby causing discomfort, urine leaking, soiling, and embarrassment, etc. These problems are aggravated when the person is active and mobile during such daily activities as walking, running, driving, and like physical work, etc.

Further problems relate to the emptying of the known reservoir of urine, as well as with the attachment of the reservoir to the thigh or upper leg. Either the person has to undress in order to empty the reservoir, or the person has to wear loosely-fitting pants to allow the person to roll up a pants leg enough to gain access to the reservoir. Both methods are cumbersome and not always comfortable. Moreover, if a man has to drain the reservoir in a public restroom, then he is faced with an embarrassing situation.

Another disadvantage is that there is insufficient support for the known reservoir beyond the straps fitted around the thigh or upper leg. The straps are both tight and uncomfortable, yet insecure, i.e., the straps tend to restrict blood circulation, yet could not always prevent the reservoir from eventually slipping down the leg. Also, the known reservoir prevents the person from wearing ordinary, closely-fitted street clothes, because the reservoir outline could show through the clothes, and because the pants leg could not be rolled up high enough to allow the person to gain ready access to the reservoir.

The drain on these known reservoirs also presents problems to some people. Individuals with shaky or arthritic hands or with neurologic pathologies, or some elderly, young, or handicapped, individuals, might have difficulty removing a plug, or screwing a cap off, or turning a valve, to open the drain, as well as with the reverse procedure to close the drain. Some people also may soil their hands, or get contaminate on adjacent body areas, while draining the reservoir. The problems of the various types of existing drainage catheters may be so great that some people may have difficulty in coping with them. Hence, in those instances, the only alternative is to wear bulky and embarrassing diapers, or to refuse to go out in public at all. For all these reasons, the urine-incontinent man or woman is often severely handicapped in both his economic and social life.

Accordingly, there is a need for a catheter system that is simple to use, and that alleviates the above problems.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The structural components of the catheter system have been represented where appropriate by conventional symbols in the drawings, showing only those specific details that are pertinent to understanding the embodiments of the present invention so as not to obscure the disclosure with details that will be readily apparent to those of ordinary ski in the art having the benefit of the description herein.

DETAILED DESCRIPTION

Referring now to FIGS. 1-6 of the drawings, one embodiment of a catheter system 10 comprises an indwelling, hollow catheter 12, typically constituted of a silicone material, or a coated natural latex material, or any medical grade material, having a generally cylindrical tip 14 inserted through a person's urethra and into the person's bladder in use, and at least two main and auxiliary, generally cylindrical, separate lumens 26, 28 having interior channels. The tip 14 has an opening 16 through which urine from the bladder passes through the urethra and into the main lumen 26 of the catheter 12 to a urine drainage port 30. The catheter 12 may have an optional, expandable balloon 34 adjacent the tip 14. The auxiliary lumen 28 may also have a fill port 32 through which a fluid, typically sterile water, is admitted to fill and expand the balloon 34 to its illustrated dashed line shape in FIG. 1 in order to anchor the tip 14 in the person's body. The fill port 32 also prevents backflow of the sterile water and an unauthorized collapse of the balloon 34.

In a preferred embodiment, the balloon 34 and the auxiliary lumen 28 are eliminated. The presence of the balloon 34 has sometimes caused a small amount of residual urine, e.g., 10-100 mL, to remain in the bladder. This residual urine can become infected, thereby sometimes resulting in chronic infection and scarring of the urethra and the bladder, as well as an encrustation to form around and within the catheter 12. This can block the opening 16 and the urine flow along the catheter 12, and may result in a risk of bladder spasm, as well as in a painful medical emergency that requires a rapid medical response. When the sterile water is eventually removed from the balloon 34 with a syringe inserted through the fill port 32 prior to catheter withdrawal, the balloon 34 may sometimes fail to collapse completely. This can result in a small rim that can make it difficult or even impossible to withdraw the catheter.

In addition, the balloon 34 can sometimes break during insertion and be fragmented. Also, the balloon 34 can sometimes be expanded before complete insertion, thereby resulting in bleeding, bodily damage, and even rupture of the urethra. In long term usage, this can lead to permanent scarring of the urethral passage, for both men and women.

Figure 4:
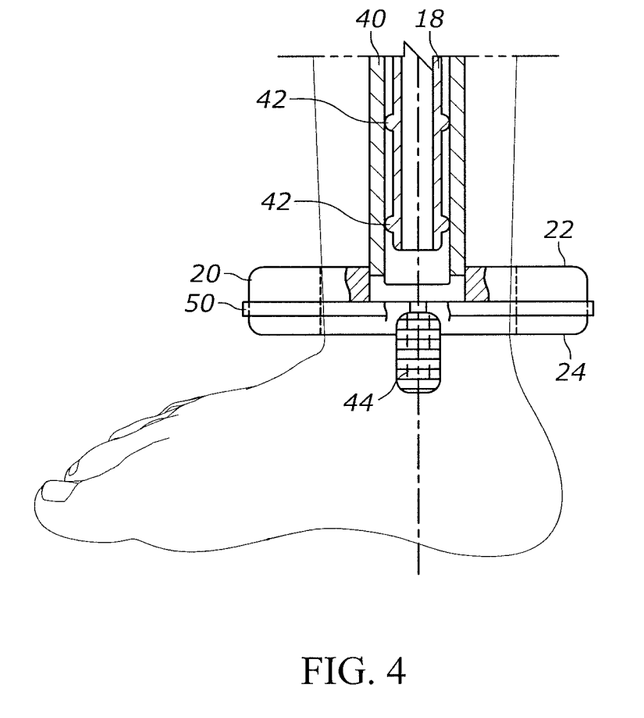
FIG. 4 is an enlarged, part-sectional, side view of additional components of the system of FIG. 1 depicting its mounting on a person's leg.
Figure 5:
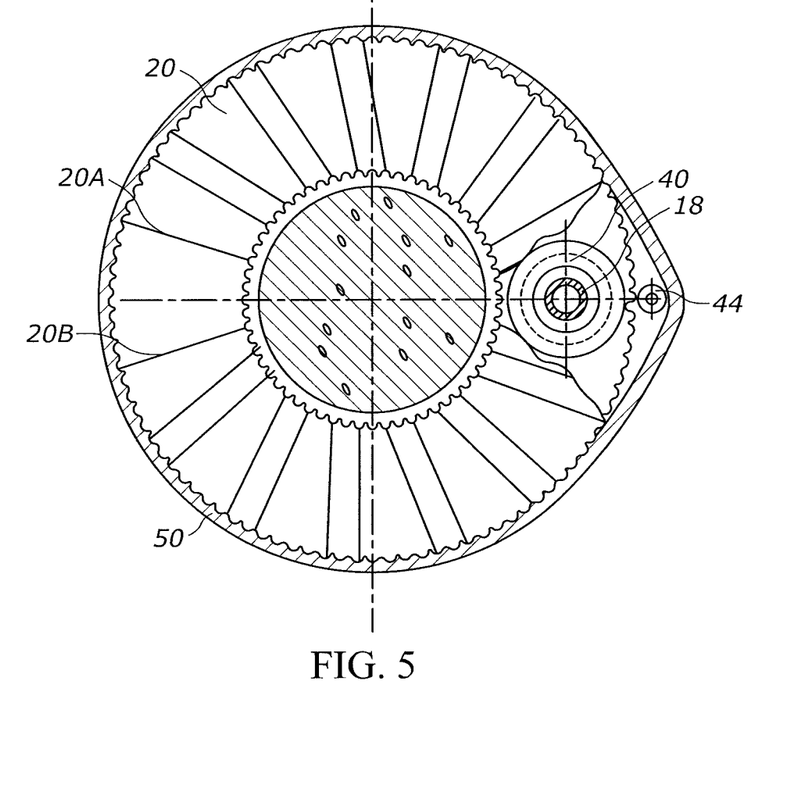
FIG. 5 is a top plan view of the components of FIG. 4 in accordance with one embodiment.
Figure 7:
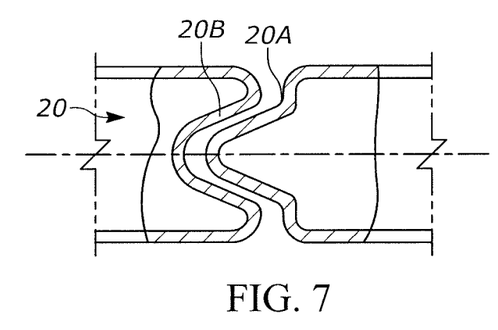
FIG. 7 is a sectional view of a modified detail of the system.

A flexible, hollow bag or reservoir 20 (see FIG. 4), typically constituted of a plastic material and configured as a cylinder, is advantageously bendable from an initial linear shape to a final curved, generally annular shape. Alternatively, the reservoir 20 may already be pre-formed into the curved annular shape. In use, the reservoir 20 extends circumferentially at least partially around the person's ankle and has walls bounding an interior compartment. As shown in FIG. 5, the curved reservoir 20 has opposite ends 20A, 20B that are spaced apart in the final shape. As shown in FIG. 7, the bent reservoir 20 has opposite ends 20A, 20B that engage each other, and may even interconnect with each other, for example, with a press fit or a snap fit, in order to keep the final shape around the ankle. As shown in FIG. 4, the walls of the reservoir may be smooth, or may be corrugated to facilitate the bending into the curved shape as shown in FIG. 5. The corrugated walls permit the reservoir 20 to be stretched and collapsed, as needed, during installation on the person.

A flexible, elongated, cylindrical tube 18, also typically constituted of a plastic medical grade material, has one end press-fitted to the urine drainage port 30 of the catheter 12, and an opposite end connected, as described below, to, and in fluid communication with, the reservoir 20. The tube 18 is hollow for conducting urine in the catheter 12 through the tube 18 into the interior compartment of the reservoir 20. The length of the tube 18 may be adjusted to fit different persons whose legs are of different lengths by cutting the tube 18 to a desired length. One of the walls of the reservoir 20 is a top wall 22, and another of the walls of the reservoir 20 is a bottom wall 24 that engages and rests on a top of the person's foot in use to resist downward movement of the reservoir 20 as the reservoir is filled with urine.

Figure 1:
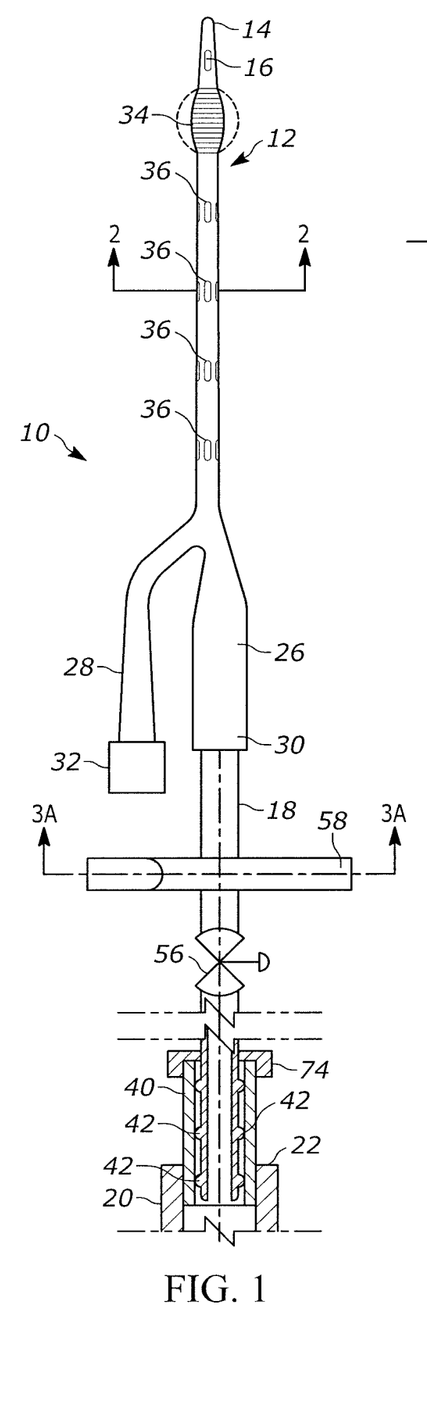
FIG. 1 is a broken-away, part-sectional, reduced-scale, side view of one embodiment of some components of a catheter system in accordance with this disclosure.
Figure 2:
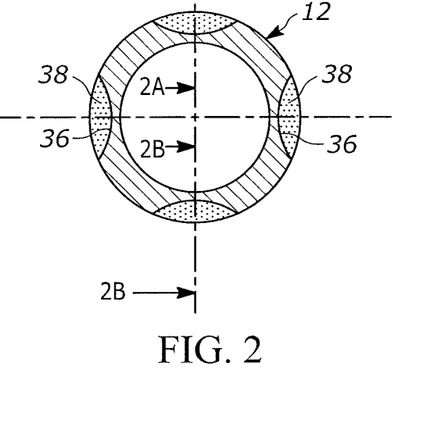
FIG. 2 is an enlarged sectional view taken on line 2-2 of FIG. 1.
Figure 2A:
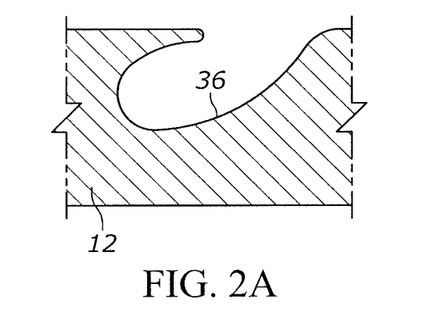
FIG. 2A is an enlarged sectional view of a modified detail taken on line 2A-2A of FIG. 2.
Figure 2B:
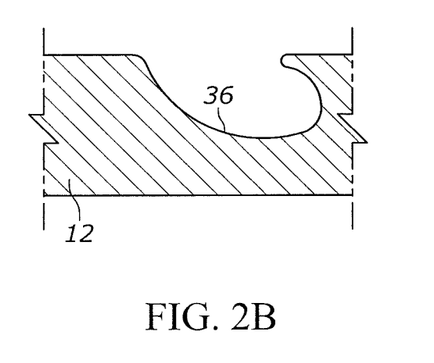
FIG. 2B is an enlarged sectional view of a modified detail taken on line 2B-2B of FIG. 2.

Advantageously, the catheter 12 has at least one pocket, and preferably a plurality of pockets 36, each filled with a lubricant 38 (see FIG. 2) to ease insertion and decrease friction of the catheter 12 through the urethra and into the bladder. As shown in FIG. 1, the pockets 36 may be spaced apart lengthwise along an axis of the catheter 12 and/or circumferentially around the catheter 12. As shown, each pocket 36 is a crater, preferably having a parabolic shape, for holding a maximum amount of the lubricant 38, which is beneficial for long term usage and to decrease friction between the catheter 12 and the urethral passage. It will be understood that any other shape for the pocket 36 may be employed. For example, see FIGS. 2A, 2B, wherein the lubricant pockets 36 are asymmetrical and oriented at different opposite angles of inclination relative to the axis to facilitate long term retention of the lubricant 38 in the pockets 36. In addition, a surface coating, such as a polytetrafluoroethylene, a hydrogel, or a silicon elastomer, may be applied over the exterior of the catheter 12, again to ease insertion and decrease friction.

A rigid, tubular, hollow, cylindrical sleeve 40, which is elongated along a longitudinal sleeve axis, is inserted into, and extends through, the top wall 22 into the compartment of the reservoir 20, and is securely held therein, preferably with a press fit or a snap fit. The opposite end of the tube 18 is cut, as described above, to accommodate and fit different persons having legs of different lengths. The opposite cut end of the tube 18 may be inserted into an upper end of the sleeve 40, and/or through a sealing cap 74, and is free to move and slide along the longitudinal sleeve axis as the person moves his legs and body, e.g., during his daily activities. The cap 74 serves to seal the interior of the sleeve 40.

Advantageously, the opposite end of the tube 18 has at least one annular barrel or slide collar 42, and preferably a plurality of annular barrels or slide collars 42 that are spaced apart along the longitudinal sleeve axis. The collars 42 make a sliding, sealing contact with the interior wall of the sleeve 40 and serve as an automatic length compensator to accommodate relative movement between the tube 18 and the sleeve 40 during the person's movement. The collars 42 also serve to reduce friction between the tube 18 and the sleeve 40 during their relative movement.

Figure 8:
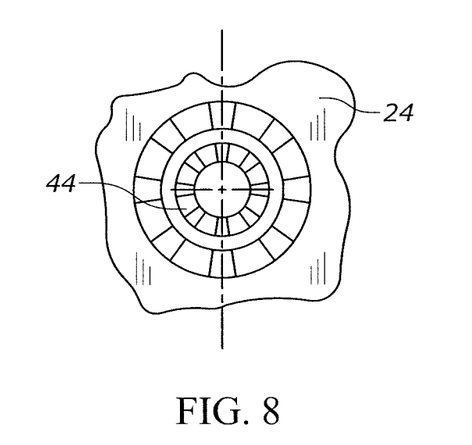
FIG. 8 is an enlarged bottom plan view of another detail of the system.
Figure 9:
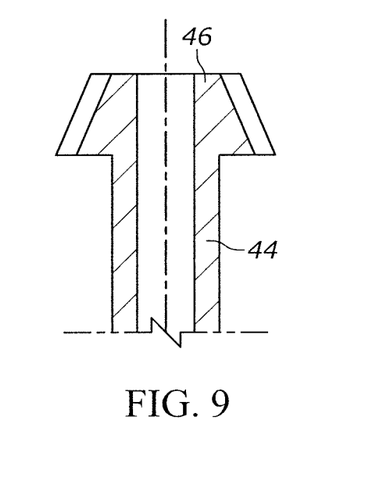
FIG. 9 is an enlarged sectional view of another detail of the system.

A flexible, tubular, hollow, drain pipe 44 (see FIG. 6), preferably constituted of a corrugated plastic material, extends between an inlet pipe end 46 and its opposite outlet pipe end 48. The inlet pipe end 46 is inserted into, and extends through, the bottom wall 24 into the compartment of the reservoir 20, and is securely held therein, preferably with a press fit or a snap fit. As shown in FIG. 9, the inlet pipe end 46 preferably has a frustoconical shape. As shown in FIG. 8, the bottom wall 24 has an opening in which the inlet pipe end 46 is received, and radial slits bound the opening so as to closely engage and fluid-tightly seal the pipe end 46 and prevent its accidental disconnection.

Figure 6:
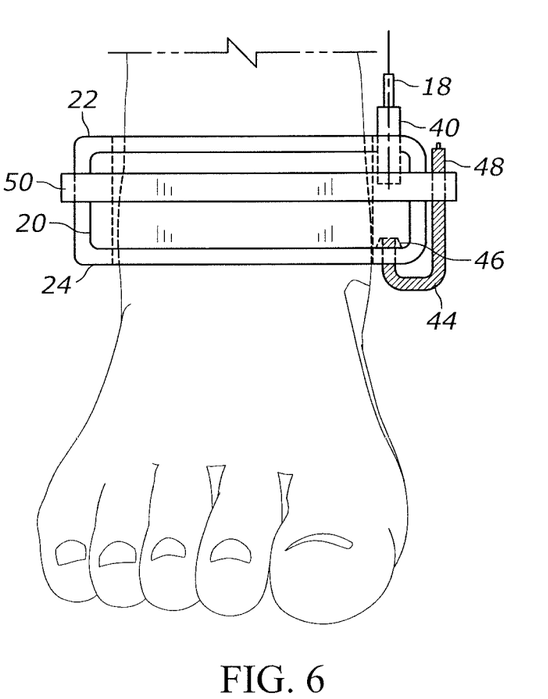
FIG. 6 is a broken-away, front elevation view of the components of FIG. 4 mounted on the person's leg.

The drain pipe 44 is flexed and manipulated in any direction in use so as to move the outlet pipe end 48 relative to the inlet pipe end 46 between a raised position above the bottom wall 24 as shown in FIG. 6, and a lowered position in which the outlet pipe end 48 is positioned below the bottom wall 24 in order to empty the compartment of the reservoir 20 of urine. The corrugated drain pipe 44 may be stretched (expanded) and collapsed (retracted), as needed, during movement between the raised and lowered positions.

Figure 6A:
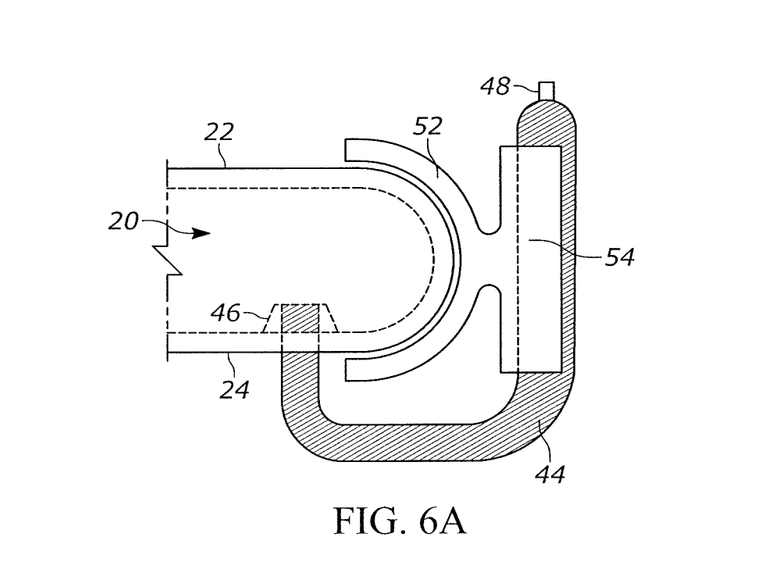
FIG. 6A is a broken-away, side view of a modified detail of the system.

An elastic, endless band 50 surrounds the outlet pipe end 48 to hold the outlet pipe end 48 in its raised position as the stretched elastic band 50 seeks to return to its original shape. Alternatively, the band 50 may be a belt having hook-and-loop fasteners. When it is desired to empty the reservoir 20, the band 50 is moved to expose and release the outlet pipe end 48 for manipulation and movement. Similarly, the band 50 also surrounds the reservoir 20 to hold the reservoir 20 in its final shape and in its mounted position atop the person's foot. In a variant construction, as shown in FIG. 6A, a bracket 52 may be positioned and held at a side of the reservoir 20. The bracket 52 has a pair of side arms 54 bounding a U-shaped channel in which the drain pipe 44 may be snapped in place and secured in the raised position, as well as being readily unsnapped in order to move the outlet pipe end 48 to the lowered position.

Figure 6B:
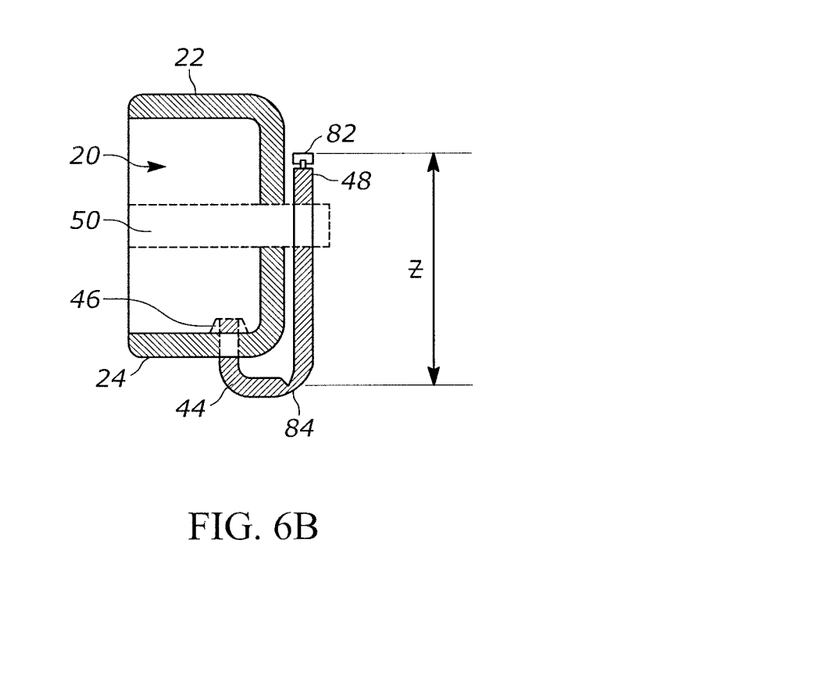
FIG. 6B is a broken-away, side view of a modified detail of the system.
Figure 6C:
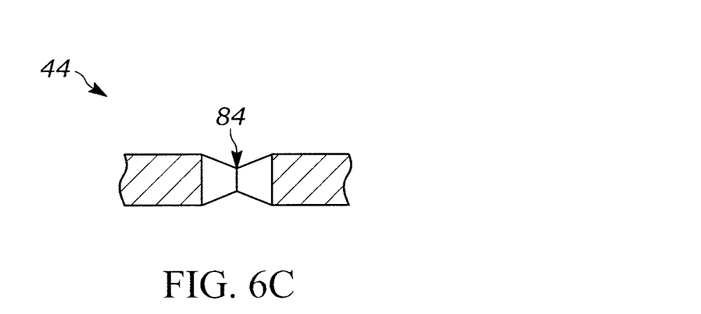
FIG. 6C is a broken-away, side view of a modified detail of FIG. 6B.

As best shown in FIG. 6B, the outlet pipe end 48 of the drain pipe 44 may be closed with a removable cap 82. In addition, the drain pipe 44 may advantageously be formed with a bending line 84 intermediate its ends 46, 48. In the raised position shown in FIG. 6B, the drain pipe 44 is kinked at the bending line 84, thereby shutting off any urine flow towards the outlet pipe end 48. When the outlet pipe end 48 is lowered by being moved over the distance "Z" in FIG. 6B, then the drain pipe 44 is unkinked, as shown in FIG. 6C, in which case, urine is free to flow towards the outlet pipe end 48.

Figure 3A:
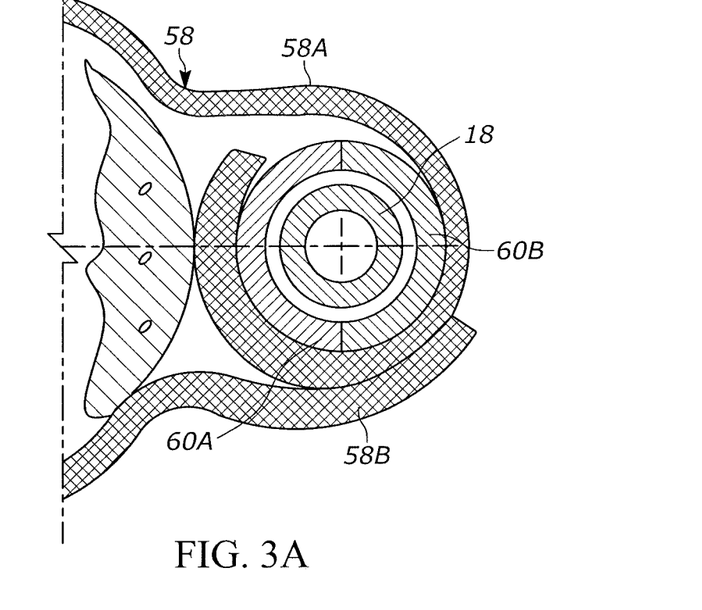
FIG. 3A is an enlarged sectional view taken on line 3A-3A of FIG. 1.

Returning to FIG. 1, a manual valve 56 may be positioned anywhere along the tube 18, typically positioned below the person's knee, to control the urine flow. Also, a guide strap 58 encircles the person's leg, and is typically positioned below the person's knee. As best shown in FIG. 3A, the guide strap 58 has two opposite strap ends 58A, 58B having mutually contacting U-shaped members 60A, 60B between which the tube 18 is received with mechanical clearance, thereby allowing the tube 18 to have freedom of movement and to be freely guided when the strap ends 58A, 58B are fastened together, for example, with hook-and-loop fasteners, such as Velcro (trademark).

Figure 10:
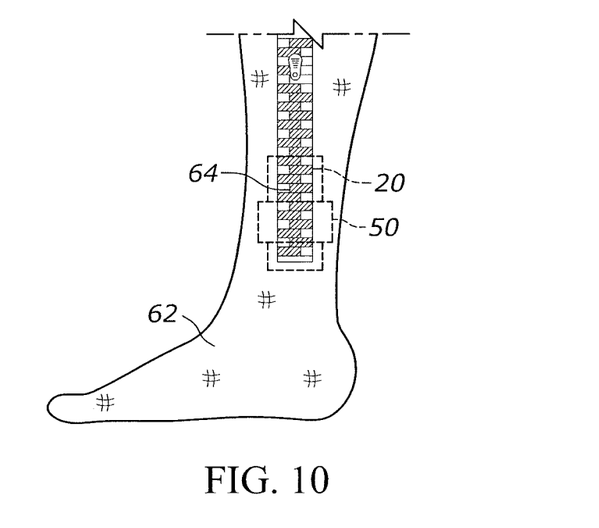
FIG. 10 is a side view of another modified detail of the system.

Instead of the endless band 50, a stocking 62 (see FIG. 10) may be worn over the reservoir 20 and the drain pipe 44, in order to enclose and hold the reservoir 20 in its final shape and in its mounted position atop the foot and around the ankle, as well as to hold the outlet pipe end 48 in its raised position. The stocking 62 has an openable fastener, such as a zipper 64 that, when opened, allows ready access to the outlet pipe end 48 of the drain pipe 44.

Figure 11:
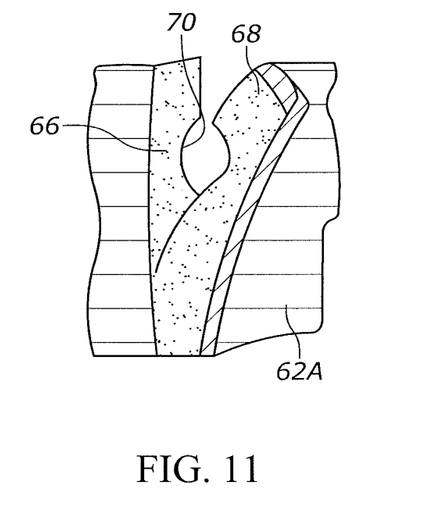
FIG. 11 is a broken-away, enlarged side view of a further modified detail of the system.
Figure 12:
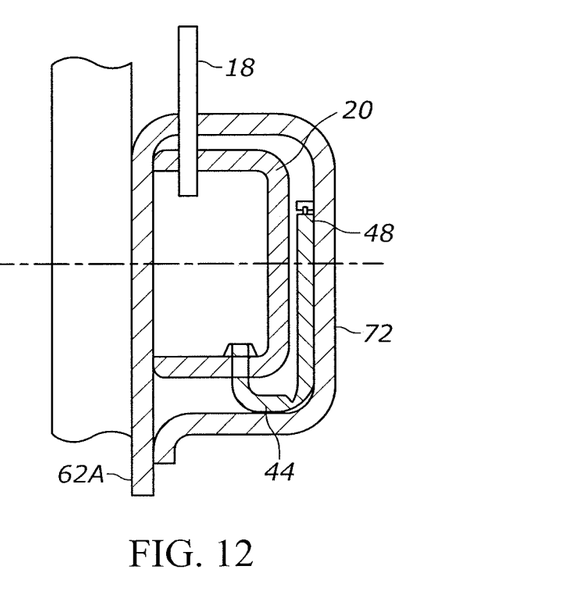
FIG. 12 is a broken-away, sectional view of the detail of FIG. 11.

Instead of the zipper 64, the fastener may comprise a pair of hook-and-loop fasteners 66, 68, such as Velcro (trademark), as shown in FIGS. 11-12, on neck portions of a stocking 62A that is worn under the reservoir 20 to prevent skin irritation from the reservoir 20. The neck portions form an opening 70 therebetween. The tube 18 is received in the opening 70 in use. The upper annular neck of the stocking 62A is folded over to form an annular cuff 72 that surrounds and holds the outlet pipe end 48 in its raised position, and also surrounds and holds the reservoir 20 in its final shape and in its mounted position atop the foot and around the ankle.

Figure 13:
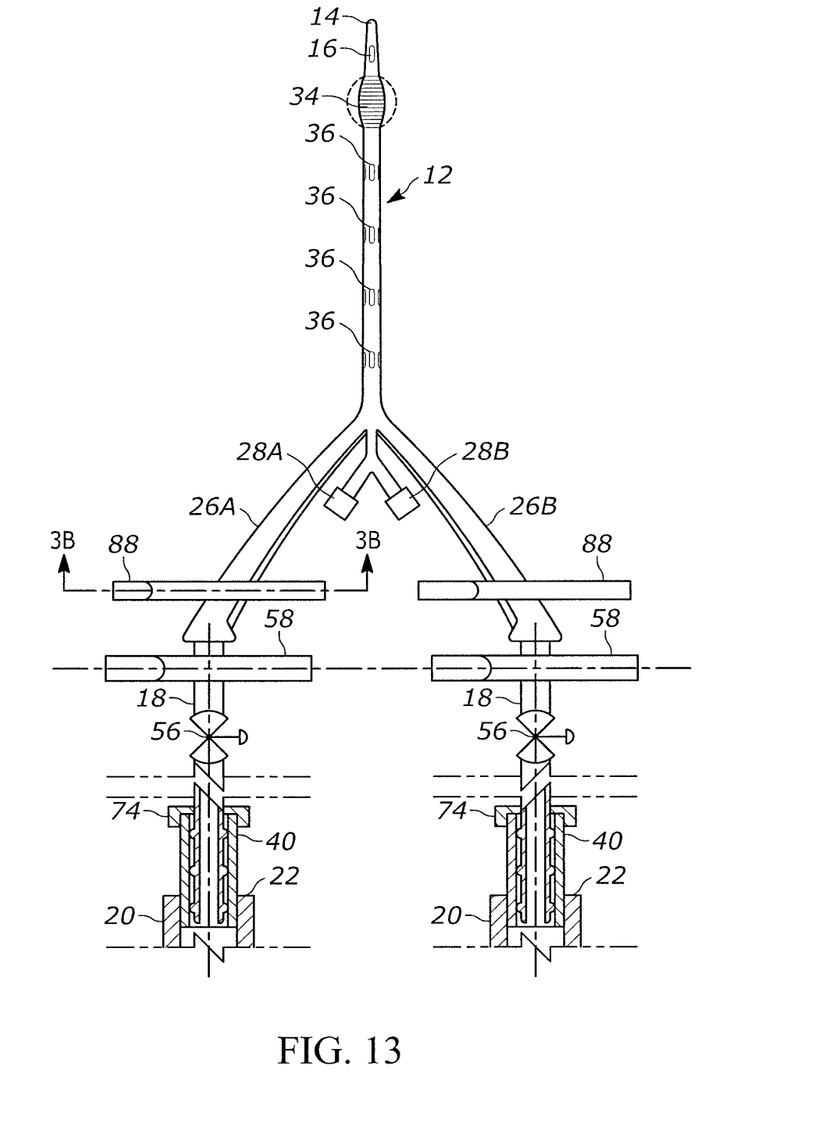
FIG. 13 is a broken-away, part-sectional, reduced-scale, side view of another embodiment of some components of a catheter system in accordance with this disclosure.

FIG. 13 depicts another embodiment of a urine collection and drainage system that is analogous to that shown in FIG. 1, and hence, like reference numerals have been used to identify like parts. Instead of one main lumen 26 and one auxiliary lumen 28, the embodiment of FIG. 13 depicts two main lumens 26A, 26B and two auxiliary lumens 28A, 28B. The main lumens 26A, 26B are routed to the person's right and left legs. This allows any desired distribution, for example, an equal distribution, of urine to the right and left legs to maximize the capacity of the urine being collected. Valves 56 on the main lumens 26A, 26B may be operated to redirect the urine flow as needed to the reservoir on each leg, as well as in the event of malfunction of the main lumens 26A, 26B. One of the auxiliary lumens 28A, 28B may be used to expand the balloon 34, while the other auxiliary lumen may be used to inject medications.

Figure 3B:
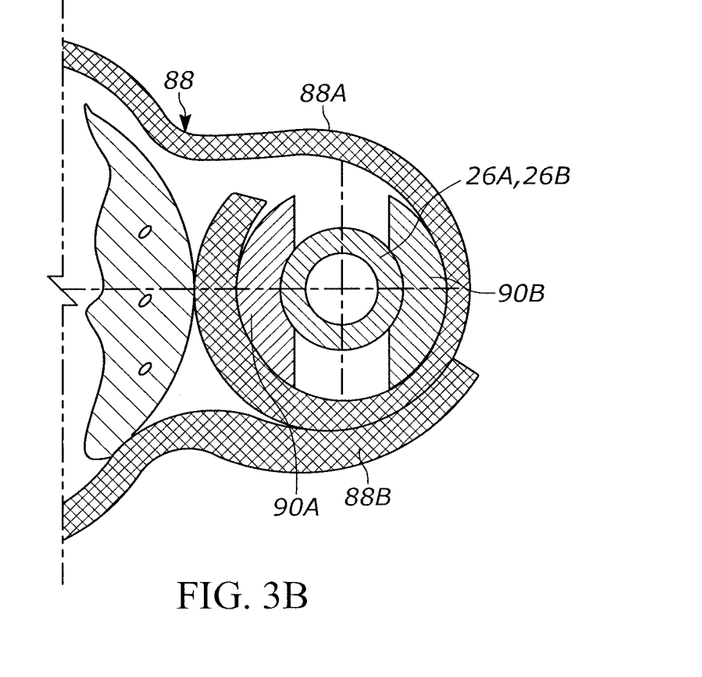
FIG. 3B is an enlarged sectional view taken on line 3B-3B of FIG. 13.

As also shown in FIG. 13, a holding strap 88 encircles the person's leg, and is typically positioned above each person's knee. As shown in FIG. 3B, each holding strap 88 has two opposite strap ends 88A, 88B having a pair of U-shaped members 90A, 90B that are spaced apart and that clamp each main lumen 26A, 26B therebetween in a fixed position when the strap ends 88A, 88B are fastened together, for example, with hook-and-loop fasteners, such as Velcro (trademark). The holding straps 88 are used to help anchor the main lumens 26A, 26B on the person's leg, in order to prevent the catheter 12 from being pulled down.

As previously mentioned, the balloon 34, which is known in the art, is preferably eliminated to avoid the aforementioned problems. The resting of the reservoir 20 atop the person's foot, the holding straps 88, and the compensating relative movement between the tube 18 and the sleeve 40 all serve to prevent the urine-filled weighted reservoir 20 from pulling the catheter 12 down.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing," or any other variation thereof, are intended to cover a non-exclusive inclusion, such that a process, method, article, or apparatus that comprises, has, includes, or contains a list of elements does not include only those elements, but may include other elements not expressly listed or inherent to such process, method, article, or apparatus. An element proceeded by "comprises . . . a," "has . . . a," "includes . . . a," or "contains . . . a," does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting embodiment the term is defined to be within 10%, in another embodiment within 5%, in another embodiment within 1%, and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A catheter system comprising:
   an indwelling, hollow catheter having a tip inserted into a person's bladder, the tip having an opening through which urine from the bladder passes into the catheter, wherein the catheter includes a catheter wall defining at least one pocket for the retention of lubricant including a pocket opening defined on a surface of the catheter wall and a cavity extending into the catheter wall, wherein a first portion of the pocket opening overhangs the cavity and a second portion of the pocket opening does not overhang the cavity to create an asymmetrical parabolic shaped cavity;
   a flexible reservoir extending around the person's ankle and having walls bounding an interior compartment; and
   a flexible, elongated tube having one end connected to the catheter and an opposite end connected to the reservoir, the tube being hollow for conducting the urine in the catheter through the tube into the compartment of the reservoir;
   wherein one of the walls of the reservoir is a bottom wall that engages and rests on a top of the person's foot in use to resist downward movement of the reservoir as the reservoir is filled with the urine.

2. The system of claim 1, wherein the at least one pocket is filled with a lubricant to ease insertion and decrease friction of the catheter.

3. The system of claim 1, the catheter wall defines a first asymmetrical parabolic shaped cavity angled at a first inclination angle relative to an axis of the catheter, and a second asymmetrical parabolic shaped cavity angled at a second inclination angle relative to an axis of the catheter, wherein the first inclination angle is different than the second inclination angle.

4. The system of claim 1, wherein the reservoir is bendable from an initial linear shape to a final curved shape.

5. The system of claim 4, wherein the reservoir has opposite ends that are spaced apart in the final curved shape.

6. The system of claim 4, wherein the reservoir has opposite ends that engage each other in the final curved shape.

7. The system of claim 1, wherein the walls of the reservoir are smooth.

8. The system of claim 1, wherein the walls of the reservoir are corrugated.

9. The system of claim 1, wherein another of the walls of the reservoir is a top wall, and a rigid, tubular, hollow sleeve extending along a longitudinal axis through the top wall into the compartment and securely held, and wherein the opposite end of the tube is mounted within the sleeve for freedom of movement along the longitudinal axis.

10. The system of claim 1, wherein the opposite end of the tube has at least one annual slide collar.

11. The system of claim 1, further comprising a flexible drainpipe having an inlet end in fluid communication with the compartment of the reservoir, and an outlet end movable between a raised position above the bottom wall and a lowered position below the bottom wall.

12. The system of claim 11, wherein the flexible drainpipe is elongated, has a corrugated wall, is expandable and retractable in length and is freely manipulatable.

13. The system of claim 11, further comprising a band surrounding the reservoir to hold the reservoir in a final shape atop the person's foot and to hold the outlet end in the raised position.

14. The system of claim 11, further comprising a bracket at a side of the reservoir, the bracket having a channel to hold the outlet end in the raised position.

15. The system of claim 11, wherein the drainpipe has a bending line about which the drain pipe is bent between a kinked position in which the urine is prevented from flowing to the outlet end and an unkinked position in which the urine is permitted to flow to the outlet end.

16. The system of claim 11, wherein the inlet end has a frustoconical shape, and wherein the bottom wall has radial slits bounding an opening in which the frustoconical inlet end is received.

17. The system of claim 1, and a guide strap encircling the person's leg and the tube, and wherein the guide strap has a pair of U-shape members that receive the tube with clearance.

18. The system of claim 1, and a holding strap encircling a person's leg and the catheter, and wherein the strap has a pair of U-shaped members that clamp the catheter therebetween in a fixed position.

19. The system of claim 1, further comprising a valve on the tube for controlling the urine.

20. The system of claim 1, and a fill port for injecting medication into the catheter.

21. The system of claim 1, wherein the catheter has an expandable balloon adjacent to the tip, and a fill port through which a fluid is admitted to fill and expand the balloon in order to anchor the tip in the person's bladder.

22. A catheter comprising:
   a catheter wall defining a lumen extending between a tip and a drainage port, the catheter wall defining at least one pocket for the retention of lubricant including a pocket opening defined on a surface of the catheter wall and a cavity extending into the catheter wall, wherein a first portion of the pocket opening overhangs the cavity and a second portion of the pocket opening does not overhang the cavity to create an asymmetrical parabolic shaped cavity.

23. The catheter of claim 22, wherein the catheter wall defines a first asymmetrical parabolic shaped cavity angled at a first inclination angle relative to an axis of the catheter, and a second asymmetrical parabolic shaped cavity angled at a second inclination angle relative to an axis of the catheter, wherein the first inclination angle is different than the second inclination angle.

24. A catheter comprising:
a catheter wall defining a first asymmetrical parabolic shaped cavity angled at a first inclination angle relative to an axis of the catheter, and a second asymmetrical parabolic shaped cavity angled at a second inclination angle relative to an axis of the catheter, wherein each of the first and second asymmetrical parabolic shaped cavity include a pocket opening defined on a surface of the catheter wall and a cavity extending into the catheter wall, wherein a first portion of the pocket opening overhangs the cavity and a second portion of the pocket opening does not overhang the cavity to create an asymmetrical parabolic shaped cavity, and wherein the first inclination angle is different than the second inclination angle.

* * * * *